(12) United States Patent
Kamiyama

(10) Patent No.: US 6,673,019 B2
(45) Date of Patent: Jan. 6, 2004

(54) DIAGNOSTIC ULTRASOUND IMAGING BASED ON RATE SUBTRACTION IMAGING (RSI)

(75) Inventor: Naohisa Kamiyama, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/772,900

(22) Filed: Jan. 31, 2001

(65) Prior Publication Data

US 2002/0028994 A1 Mar. 7, 2002

(30) Foreign Application Priority Data

Jan. 31, 2000 (JP) ................................ P. 2000-023152

(51) Int. Cl.[7] .............................................. A61B 8/00
(52) U.S. Cl. .................................................... 600/443
(58) Field of Search ............................... 600/443, 447, 600/458, 437

(56) References Cited

U.S. PATENT DOCUMENTS

| | | | | |
|---|---|---|---|---|
| 5,456,257 A | * | 10/1995 | Johnson et al. | 600/458 |
| 5,577,505 A | * | 11/1996 | Brock-Fisher et al. | 600/458 |
| 5,632,277 A | * | 5/1997 | Chapman et al. | 600/443 |
| 5,706,819 A | * | 1/1998 | Hwang et al. | 600/458 |
| 5,718,229 A | * | 2/1998 | Pesque et al. | 600/441 |
| 5,833,613 A | * | 11/1998 | Averkiou et al. | 600/447 |
| 5,879,303 A | * | 3/1999 | Averkiou et al. | 600/447 |
| 6,036,643 A | * | 3/2000 | Criton et al. | 600/454 |
| 6,074,348 A | * | 6/2000 | Chiao et al. | 600/443 |
| 6,406,430 B1 | * | 6/2002 | Ishrak et al. | 600/441 |

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

In a diagnostic ultrasound apparatus, an ultrasound pulse signal is transmitted two times in each of the rasters on a region to be scanned. Subtraction between echo signals received at each time of transmission is made to obtain a difference signal. Either one of the echo signals and the difference signal are produced into individual tomographic images, independently of each other. The produced individual tomographic images are displayed with a superposed manner one on the other or parallel-arranged manner. This allows contrast echo imaging to be conducted on a rate subtraction imaging technique. Minute blood flows are depicted distinguishably from tissue surrounding those flows in a steady manner.

38 Claims, 10 Drawing Sheets

TM2 + TMs

TM2 + TMs

DIAGNOSTIC ULTRASOUND IMAGING BASED ON RATE SUBTRACTION IMAGING (RSI)

BACKGROUND OF THE INVENTION

1. Field of the Invention

The present invention relates to diagnostic ultrasound imaging by which imaging is performed based on a contrast echo technique for an object into which an ultrasound contrast agent of which main constituent is microbubbles is administered. In particular, the present invention relates to diagnostic ultrasound imaging capable of separating transient signals caused due to the microbubbles of the ultrasound contrast agent on the basis of a rate subtraction imaging (RSI) technique.

2. Description of the Related Art

Ultrasound signals have been clinically used in various fields, and one field is an application to diagnostic ultrasound apparatus. A diagnostic ultrasound apparatus acquirers an image signal through transmission and reception of an ultrasound signal toward and from an object and is used in a variety of modes utilizing non-invasiveness of the signal.

One typical type of diagnostic ultrasound apparatus produces tomographic images of a soft tissue of a living body by adopting ultrasound pulse reflection imaging. This imaging method is noninvasive and produces tomographic images of the tissue. Compared with other medical modalities such as diagnostic X-ray imaging, X-ray CT imaging, MRI, or diagnostic nuclear medicine imaging, this pulse reflection imaging has many advantages: real-time display is possible, a compact and relatively inexpensive apparatus can be constructed, patient's exposure to X-rays or others will not occur, and blood imaging is possible thanks to ultrasound Doppler imaging. This imaging is therefore widely used for diagnosis of the heart, abdomen, mammary gland, and urinary organs, and for diagnosis in obstetrics and gynecology. In particular, pulsation of the heart or motion of a fetus can be observed in real time through manipulation that is as simple as just placing an ultrasound probe on a patient's body surface. Moreover, since patient's X-ray exposure need not be cared about, screening can be carried out many times repeatedly. There is also the advantage that the apparatus can be moved to a bedside position for ready screening.

In the field of the ultrasound diagnosis, a trans-venous injection type of ultrasound contrast agent has been commercially available. This agent, which is injected into an object through the vein in screening the heart or organs in the abdomen, is used to enhance echo signals emanated from flows of blood so as to evaluate blood flow kinetics. This imaging is known as contrast echo imaging. Since the trans-venous injection of the contrast agent is less expensive than its trans-arterial injection (i.e., trans-arterial injection type of contrast echo imaging), diagnosis based on the trans-venous injection has been spotlighted. The main constituent of the contrast agent is microbubbles that act as sources to reflect ultrasound waves. The larger the amount or concentration of an injected contrast agent is, the larger the contrast effect is. However, the microbubbles are delicate substances, so they are characteristic of collapse due to irradiated ultrasound waves. It has been found that various conditions, such as, an extremely shortened duration of the contrast effect resulted from a certain condition of ultrasound waves, will occur. Although a contrast agent of high persistency and high durability has been developed recently, the collapse phenomenon of the contrast agent cannot be avoided fundamentally, because its main constituent is microbubbles. Meanwhile, the long-term persistence of the contrast agent in a human body may raise the problem of invasiveness.

In the contrast echo imaging, a contrast agent (i.e., microbubbles) is successively supplied into a region of interest of an object through blood flow. Hence, it is assumed that, even when once bubbles existing within the region collapsed by irradiated ultrasound waves, the contrast effect will be maintained as long as new microbubbles will inflow into the region of interest at the next timing of ultrasound irradiation. However, ultrasound waves are normally transmitted and received as many times as a few thousands per second, there is organ parenchyma whose blood flow speed is rather slow, and there is blood kinetics in relatively thin blood vessels. Considering these conditions, microbubbles will collapse in turn before observing on a diagnostic image intensified intensity of data due to a contrast agent, thus the contrast effect being lessened instantaneously. Various reports concerning this collapse phenomenon of microbubbles have already been published and flush echo imaging (FEI) which will be described later belongs to the imaging techniques based on the collapse phenomenon.

Of diagnostic techniques using the contrast agent, the most fundamental diagnostic technique is to detect whether or not there is blood flow in a region to be diagnosed by examining the existence of intensified intensity data depending on the contrast agent. More advanced diagnostic techniques include a technique of detecting temporal changes in spatial distributions of the contrast agent from spreads of changes in intensity or from degrees of intensified intensity data in a diagnostic region. Also included is a technique of acquiring an interval from the start of injection of a contrast agent to its arrival at a region of interest (ROI) and temporal changes in intensity data (Time Intensity Curve: TIC) or a maximum of intensity data, both of which is due to the contrast agent, within the ROI.

The contrast echo imaging can also be performed effectively with harmonic imaging (HI) using a non-fundamental component of ultrasound waves. The harmonic imaging is based on separation and detection of only a non-fundamental component derived due to nonlinear behaviors of ultrasound-excited microbubbles, which are main constituents of a contrast agent. Since internal organs of a living body are relatively difficult to cause nonlinear behaviors, the harmonic imaging can give contrast agent images with preferable contrast ratios.

It has been known that echo signals emanated from tissue such as internal organs include non-fundamental components (mainly, harmonic components), though it is lower in level than that emanated from the contrast agent, and the non-fundamental components are mixed with the entire received echo signal. Such harmonics from tissue are normally called as tissue harmonic signals, which give a basis to imaging, called tissue harmonic imaging (THI).

As practical techniques of detecting and imaging nonlinear signals (mainly harmonic signals), there have been known two techniques. One technique is that a high-pass type of echo filter is used to cut off a fundamental component, providing only a filtered harmonic component used for recombining images. The other is that a technique referred to as an inverted phase pulse adding technique (pulse inversion technique) is used to extract a harmonic component that is involved in recombining images.

Of these techniques, the inverted phase pulse adding technique is disclosed, for example, by U.S. Pat. No. 5,632, 277. Practically, in this imaging, two ultrasound pulses of which phase difference is 180 degrees from each other are transmitted along each raster (two times of transmission in total), resultant echo signals are received, respectively, and then the echo signals are added to produce added signals for imaging. This addition causes linear components included in the mutual echo signals to be cancelled out, because one of the echo signals is inversed in the waveform and both echo signals are added. Accordingly, a doubled harmonic component remains (180 degrees×2=360 degrees). This technique requires two pulses to be transmitted and received for each raster, thus a frame rate is reduced. However, design of filters is easy, even if the high-pass type of filter is used. In addition, a transmission pulse of which bandwidth is wide can be used, increasing spatial resolution.

By the way, it has been reported that the phenomenon that the microbubbles are vanished by irradiating ultrasound waves is used for imaging called flash echo imaging (also called a transient response imaging), increasing enhancement of intensity (for instance, refer to Japanese Patent Laid-open Publication No. 8-280674). This imaging is based on the principle that, instead of the conventional continuous scan carried out at a rate of tens of frames per second, intermittent transmission is performed at a rate of one frame per a few seconds. During each interval between the two times of transmission, microbubbles are made to gather into a region to be scanned without collapses. The gathered microbubbles are then vanished at a time by the next transmission, generating an echo signal of higher intensity.

The foregoing harmonic imaging and the flash echo imaging are not conflicting techniques, but can be combined to be used together. These two imaging techniques can be classified from a viewpoint of usage as below. As to the harmonic imaging, the techniques of a) fundamental wave imaging b) harmonic imaging on filters, and c) inverted phase pulse adding technique belong to the same category. Any one technique is selected from the above imaging types a) to c) and used. On the other hand, as to the flash echo imaging, the techniques of a') continuous transmission b') flash echo imaging (that is, intermittent transmission) are provided, in which either technique a') or b') are chosen. Alternatively, any of the former techniques a) to c) and either technique a') or b') can be used together.

As described before, use of a trans-venous type of contrast agent and use of imaging, such as the harmonic imaging or flash echo imaging, in an appropriate mode make it possible to image minute blood flow, i.e., perfusion, in the tissue of an internal organ.

However, it is not always possible for the conventional imaging to provide images of the perfusion with stability, there frequently occur the following problems.

One problem is that a diagnostic performance lowers due to a tissue harmonic signal.

A tissue harmonic component generated from the tissue of an internal organ is fundamentally lower in intensity than that from a contrast agent, as described before. Actually, however, there occur situations that make blood flow diagnosis difficult. The tissue harmonic signal differs individually and there are many persons that generate echo signals of relatively larger intensities. From a viewpoint of experience, for diagnosing the liver, for example, there is known that intensities of echo signals are different largely between a region with a lesion such as hepatocirrhosis or a fatty liver and a region with no such lesion. Since the tissue harmonic signal is caused resultantly from a non-linear characteristic of transmission of ultrasound waves, it increases as the sound pressure (output) of a transmitted ultrasound pulse is raised. In contrast, an echo signal reflected by the contrast agent is apt to instantaneously vanish when the sound pressure of the transmitted ultrasound pulse is over a given value. As a result, there occurs a problem that echo intensities of an internal organ itself is raised before injecting a contrast agent. If this occurs, it is difficult to confirm whether or not echoes around thin blood vessels on images (particularly, a region with minute blood flows) acquired after the injection of the contrast agent are resulted from the contrast agent. This problem is also true of the inverted phase pulse adding technique.

A second problem concerns with optimization for generation of images and processing of display.

The steps of recombining echo signals acquired on each raster into a tomographic image and displaying the image are involved with a variety of types of processing. Conventionally, those types of processing are optimized depending on which region is diagnosed. For example, for diagnosing an internal organ of which motions are relatively slow, such as the liver, a high frame rate is not necessary, so a density of rasters are increased to raise spatial resolution. From the same reason, after-images of several past frame images are added to suppress flickers appearing on images on account of noise or others. In the case of the heart, images are subjected to spatial differentiation of their intensities in order to emphasize the boundaries of the heart walls. Processing to enhance the depiction performance of the endocardium and epicardium is carried out as well.

However, when depicting echo signals from microbubbles of a contrast agent, it is not necessarily true that the foregoing tissue depiction processing is suitable for the depiction of such echo signals and they are depicted in an optimum state. Gathered microbubbles may show tiny speckle patterns, in which the collapses of the microbubbles are also caused. Accordingly, there are some occasions in which the contrast agent, that is, minute blood flows are seen on and off with motions. By this appearance, intensity is increased due to the contrast agent and visibility is improved due to the speckle patterns. In such situations, however, if the foregoing frame after-image processing and/or differentiation are carried out, the visibility for echo signals from the contrast agent is decreased.

To overcome this problem, in the conventionally performed contrast echo imaging, conditions for producing images giving priority to behaviors of microbubbles are frequently determined based on experienced knowledge. However, in such cases, there occurs the problem that the depiction of tissue of an internal organ is largely deviated from its optimum state so that its depiction performance is remarkably deteriorated.

SUMMARY OF THE INVENTION

The present invention has been made to overcome the above problems. An object of the present invention is to provide ultrasound imaging, in which, for performing a contrast echo imaging under the injection of a contrast agent into an object to be screened, the contrast agent, i.e., minute blood flows is distinguished from the surrounding tissue with precision so as to increase a depiction performance, and the contrast agent and tissue are individually imaged in their optimum conditions so as to increase image quality, thereby improving a diagnostic performance for the minute blood flows.

In order to realize the foregoing object, a diagnostic ultrasound apparatus according to the present invention uses rate subtraction imaging (RSI) that requires subtraction raster by raster.

According to a practical configuration of one aspect of the present invention, the diagnostic ultrasound apparatus for obtaining an image of a region to be scanned by scanning an object with a beam-shaped ultrasound signal, an ultrasound contrast agent (of which main constituent is microbubbles, for example) being injected into the object, comprising: scanning means for transmitting the ultrasound signal a plurality of times in each direction composing the region to be scanned and receiving an echo signal in response to each transmission; subtracting means for obtaining a difference signal by performing subtraction between the echo signals received with two times of transmission among the plurality of times of transmission; producing mean for independently producing both of the echo signal received with any time of transmission of the plurality of times of transmission and the difference signal into individual tomographic images; and displaying means for displaying the individual tomographic images at the same time.

For example, the plurality of times of transmission is two times of transmission in each raster composing each direction. Preferably, the producing means has processing means for processing any of a first echo signal and a second echo signal received with the two times of transmission and the difference signal under processing conditions mutually independent of each other into data of two tomographic images. By way of example, the processing conditions include at least one of a reception gain, a dynamic range, cut-off frequency and bandwidth of an echo filter, and a frame-to-frame after-image processing. Further, the processing conditions may include at least one of a correction processing technique and a color encoding technique performed when mapping intensities of the echo signal on a video screen.

Furthermore, the displaying means may have means for displaying the individual tomographic images in mutually different colors.

Further, for example, the displaying means is means for displaying the individual tomographic images with either one tomographic image superposed on the other tomographic image. In this situation, displayed is the tomographic image based on the difference signal, which serves as the other tomographic image, superposed on the tomographic image based on the echo signal, which servers as the one tomographic image. Preferably, of the one and other images, either one image is displayed in gray scales and the remaining image is displayed in colors. Another preferred example is that the displaying means is means for displaying the one and other images in mutually different colors. Further, the displaying means may be means for displaying the individual tomographic images in parallel with each other on a screen.

Accordingly, for example, during a scan, a transient echo component inherent to a contrast agent is separated and extracted from an original echo signal as a difference signal based on the rate subtraction imaging. And the difference signal and the original echo signal are processed independently of each other into separate tomographic images. The tomographic images thus processed are then displayed at the same time. In other words, the transient contrast echo image and the steady tissue echo image are processed in their optimum states, respectively, and then displayed together, for example, in a superposition display mode or a parallel display mode.

Therefore, there is a fundamental difference in signal processing between the present invention and either of 1) the conventional harmonic imaging or 2) the conventional pulse inversion imaging; in 1) the conventional harmonic imaging, one type of echo signal in which a fundamental wave and non-fundamental waves are mixed together is processed through from a probe to a display, and in 2) the conventional pulse inversion imaging, two echo signals from two times of transmission are combined before a receiver, then one combined signal is processed for display. In contrast, 3) the signal processing in the present invention is equivalent to the technique that echo signals inherent to tissue and a contrast agent are subject to processing from a probe to a frame memory (data synthesizer) independently of each other, and then combined at the stage of being displayed.

It is therefore possible to not only improve both images of the contrast agent echo and tissue echo but also preventing steadily minute blood flows in tissue from being hidden by tissue echoes so that visibility is lowered. Additionally, for observing dynamics of minute blood flows in tissue under the contrast echo imaging, a tissue echo image is always provided together with a contrast echo image to be targeted. This makes easier to understand spatial locations of distributions of minute blood flows.

The imaging according to the present invention is not limited to that carried out during a scan, but can be attained after the scan (i.e., after diagnosis on the spot) through display using echo data stored after being subjected to the above processing.

In order to attain this imaging, by way of example, the producing means has image memorizing means capable of individually memorizing image data of the individual tomographic images and individually reading out the image data thereof. Preferably, the displaying means has means for individually reading out the image data of the tomographic images from the image memorizing means and means for commanding a switchover of display modes consisting of superposed display of the individual tomographic images, parallel display of the individual tomographic images, and sole display of either one of the individual tomographic images on the bases on the read-out image data. As an example, the displaying means include means for independently setting at least one of a correction processing technique and color encoding technique accordingly to which of the echo signal and the difference signal corresponds to the read-out image data and mapping the image data on a video screen.

According to another aspect of the diagnostic ultrasound apparatus of the present invention, in the apparatus configuration identical to the foregoing basic aspect, for the echo signal, there is provided addition means for obtaining an average signal by performing average between the echo signals received with two times of transmission among the plurality of times of transmission, and both of the difference signal and the average signal produced into individual tomographic images, and the individual tomographic images are displayed at the same time.

In this case, preferably, the plurality of times of transmission is two times of transmission in each raster composing each direction. It is preferred that the producing means includes processing means for processing the average signal and the difference signal with processing conditions mutually independent of each other into data of two tomographic images. Preferably, the displaying means is means for displaying the individual tomographic images in either one of a superposition manner and a parallel manner.

As another aspect of the diagnostic ultrasound apparatus of the present invention, it may be configured in a such a manner that the subtraction means is means for performing the subtraction of the echo signal received by the first-time transmission of the plurality of times of transmission and the echo signal received by any-time transmission selected from the second-time or later transmission of the plurality of times of transmission, and the addition means is means for performing the addition of the echo signal received by the first-time transmission of the plurality of times of transmission and the echo signal received by any-time transmission selected from the second-time or later transmission of the plurality of times of transmission.

In the present invention, in the foregoing first and second aspects, it may be configured such that the scanning means is means for additionally transmitting an ultrasound signal to excite the microbubbles in each direction. In this case, it is preferred that the additional transmission of the exciting ultrasound signal interleaves in time between two times of transmission selected from the plurality of times of transmission.

Furthermore, in the present invention, in the foregoing first and second aspects, it is preferable that the displaying means has means for commanding a switchover of display modes consisting of superposed display of the individual tomographic images, parallel display of the individual tomographic images, and sole display of either one of the individual tomographic images.

On the other hand, according to one aspect of an ultrasound imaging method of the present invention, there are configurations comprising the steps of: transmitting the ultrasound signal a plurality of times in each direction composing the region to be scanned and receiving an echo signal in response to each transmission; obtaining a difference signal by performing subtraction of the echo signals received with two times of transmission among the plurality of times of transmission; independently producing both of the echo signal received with any time of transmission of the plurality of times of transmission and the difference signal into individual tomographic images; and displaying the individual tomographic images at the same time.

As another mode of the configuration of the ultrasound imaging method, there may be the additional steps of calculating an average signal by performing average between the echo signals received with two times of transmission among the plurality of times of transmission; independently producing both of the difference signal and the average signal into individual tomographic images; and displaying the individual tomographic images at the same time.

Still, another mode of the configuration of the diagnostic ultrasound apparatus is provided such that the diagnostic ultrasound apparatus for obtaining an image of a region to be scanned by scanning an object with a beam-shaped ultrasound signal, an ultrasound contrast agent being injected into the object: an ultrasound probe for transmitting and receiving the ultrasound signal; a transmitter for exciting the ultrasound probe responsively to each rate pulse so as to cause the ultrasound probe to output the ultrasound signal; a receiver for delaying and adding an echo signal received by the ultrasound probe; a controller for causing the transmitter to transmit the ultrasound signal a plurality of times in each direction composing the region to be scanned and causing the receiver to receive the echo signal in response to each transmission; a subtracter for obtaining a difference signal by performing subtraction between the echo signals received with two times of transmission among the plurality of times of transmission; a producer for independently producing both of the echo signal received with any time of transmission of the plurality of times of transmission and the difference signal into individual tomographic images; and a display for displaying the individual tomographic images at the same time.

Preferably, the plurality of times of transmission is two times of transmission in each raster composing each direction. By way of example, the producer has a processor for processing any of a first echo signal and a second echo signal received with the two times of transmission and the difference signal under processing conditions mutually independent of each other into data of two tomographic images.

Still preferably, the display is configured to display the individual tomographic images with either one tomographic image superposed on the other tomographic image. Particularly, it is preferred that the display is changeable, for example, by hand, in a superposition balance of intensity when the other tomographic image is superposed on the one tomographic image. Still preferably, the echo signal experiencing the subtraction executed by the subtracter is a radio frequency signal of the echo signal before detected.

DETAILED EXPLANATION OF PREFERRED EMBODIMENTS

Figure 1:
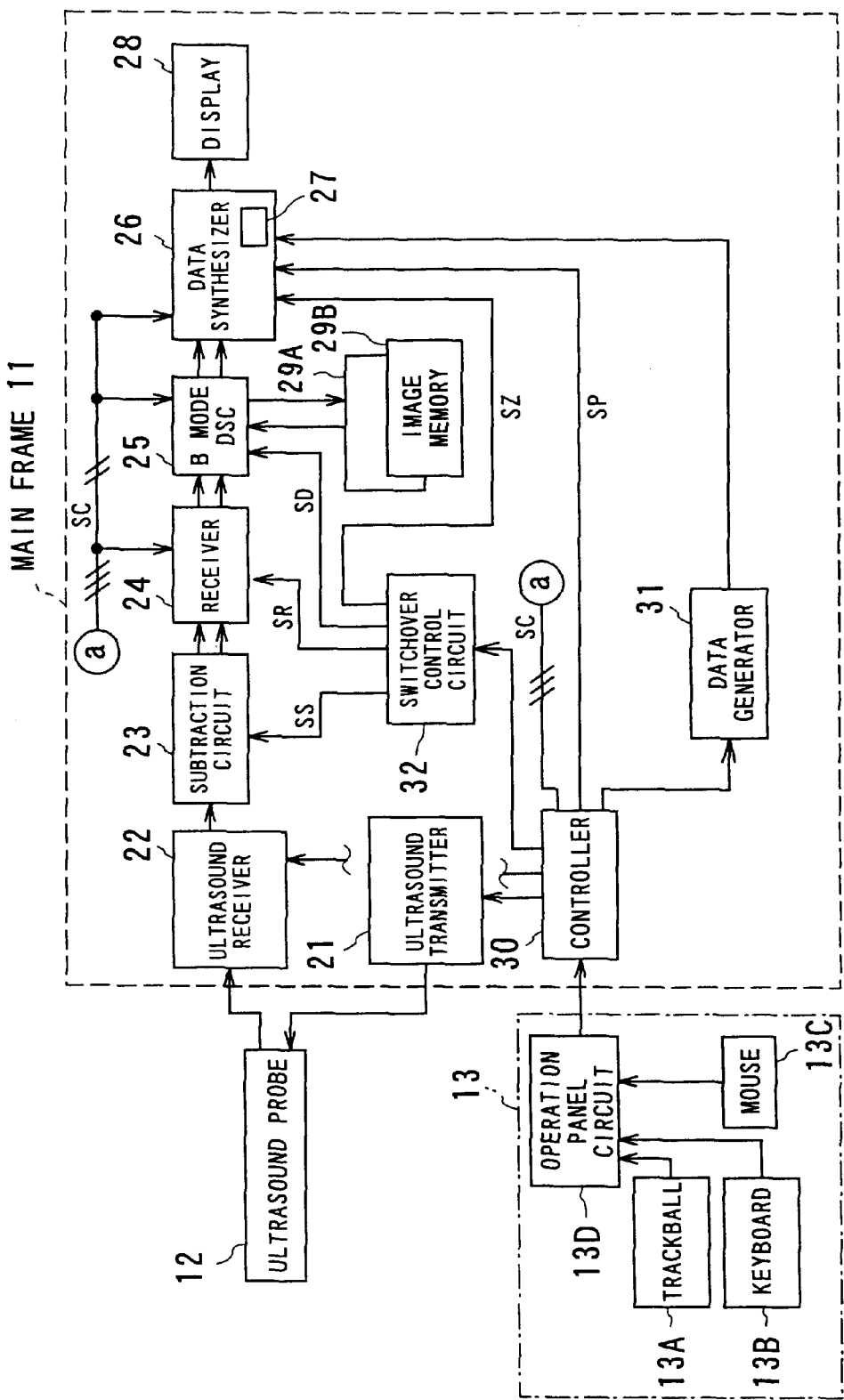
FIG. 1 is the block diagram of a diagnostic ultrasound apparatus according to embodiments of the present invention.

Referring now to the drawings, exemplary embodiments of the present invention will be described.

(First Embodiment)

Referring to FIGS. 1 to 11, a first embodiment of the present invention will now be described.

A diagnostic ultrasound apparatus according to the present invention can be applied to diagnosis of all regions of interest whose blood flow states can be observed based on contrasted degrees deriving from an injected ultrasound contrast agent into an object. The present embodiment, however, deals with a diagnostic ultrasound apparatus that has the function of identifying abnormal regions by acquiring data indicative of kinetics of blood flow on the basis of contrasted degrees of a contrast agent inflowing into the liver parenchyma or cardiac muscle (i.e. perfusion).

FIG. 1 schematically shows the entire configuration of a diagnostic ultrasound apparatus according to a first embodiment. The diagnostic ultrasound apparatus has a main unit 11, ultrasound probe 12 coupled with the main unit 11, and operation panel 13.

The operation panel 13 comprises a keyboard 13A, trackball 13B, mouse 13C, and operation panel circuit 13D. These operation devices are used by operators to input and/or set information about patients, conditions of the apparatus, and ROIs (regions of interest), like the conventional apparatus. In addition, the operation devices are used to not only set and change parameters for post-processing of signals but also select display modes, according to the present invention.

The ultrasound probe 12, which is responsible for transmitting and receiving an ultrasound signal toward and from a patient, includes piezoelectric vibrators made of piezoelectric ceramic or the like as electromechanical bilateral converting elements. For example, a plurality of piezoelectric vibrators are set in an array and incorporated in the distal part of the probe, thus constructing the phased array type probe 12. The probe 12 converts driving voltage pulses applied by the main unit 11 into ultrasound pulses and transmits them in desired directions in a region to be scanned of an object to be screened. Further, the probe 12 converts ultrasound echoes reflected from the object into electric signals with corresponding voltages.

The imaging mode employed in the main unit 11 is a "B-mode." Practically, the main unit 11 comprises an ultrasound transmitter 21 and an ultrasound receiver 22, which are connected to the probe 12. The main unit 11 also has a subtraction circuit 23, receiver 24, B-mode DSC (Digital Scan Converter) 25, data synthesizer 26 (a color coding circuit 27 installed therein), display 8, and image memories 29A and 29B, which are arranged in turn after the ultrasound receiver 22. Further, the main unit 11 has a controller 30 that receives operation signals from the operation panel 13 as well as a data generator 31 and a switchover control circuit 31 that operates in response to commands from the controller 320.

Each of the above-mentioned constituents will be described in its configuration and operations.

The ultrasound transmitter 21 has a pulse generator, transmission delay circuits, and pulsers, which are not shown. The pulse generator generates rated pulses depending on a regular pulse repetition frequency (PRF). The rated pulses are distributed by the number of transmission channels and sent to the transmission delay circuits. Timing signals used to determine delay times are sent from the controller 30 to the transmission delay circuits channel by channel. This causes the transmission delay circuits to give specified delay times to the rated pulses channel by channel. The rated pulses delayed by the specified times are then sent to the pulsers channel by channel. The pulsers generate voltage pulses and send them to each piezoelectric vibrator (each transmission channel) of the probe 12 in synchronism with each rated pulse. This makes the probe 12 irradiate ultrasound pulse waves. The waves that have been transmitted from the probe 12 are converged in the form of a beam inside the object and have a transmission directivity thereof set to a commanded scanning direction.

An ultrasound pulse signal transmitted into the object is reflected by locations of which acoustic impedance is discontinuous. Reflected ultrasound signals are received again by the probe 12 and converted into electric echo signals of corresponding voltages. The echo signals are sent from the probe 12 into the ultrasound receiver 22 for each reception channel.

The ultrasound receiver 22 is provided with preamplifiers, A/D converters, reception delay circuits, and an adder (all not shown) in this order from the input side of the receiver. The preamplifiers, A/D converters, and reception delay circuits individually include circuits assigned to all the reception channels, thus providing a digital type of ultrasound receiver. Delay times for the reception delay circuits are given by the controller 30 as delay time pattern signals in conformity with desired reception directivity. Accordingly, echo signals are, every reception channel, amplified by the preamplifiers, converted into digital signals by the A/D converters, and delay-controlled by the reception delay circuits, before being added to each other by the adder. This addition enhances echoed components from a direction according to the desired reception directivity. The transmission and reception directivities are taken into account to provide the total performance to the transmitted and received ultrasound beams.

Figure 2:
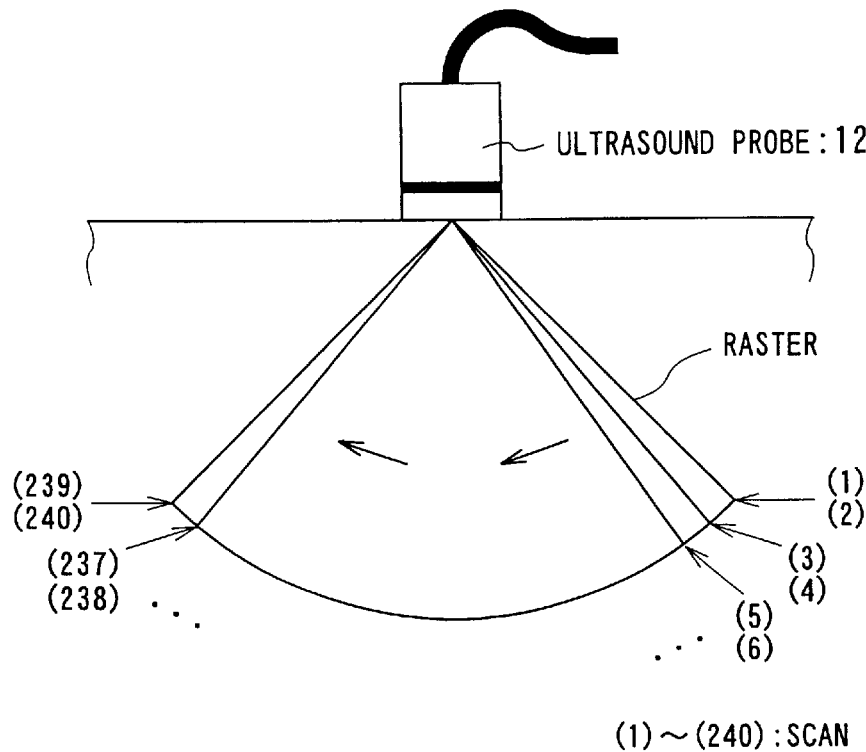
FIG. 2 shows a scan order according to a first embodiment of the present invention.

The ultrasound beam signals are, as described above, are converged into beams during their transmission and reception. Referring to FIG. 2, a scan order (transmission and reception orders of ultrasound pulse signals) for the rasters on a scanned plane of an object will now be described. As long as each of the plurality of rasters (scanning lines) that form a plane to be scanned is scanned two times, any scan order is available. In particular, it is preferable that the same raster is scanned as shorter interval of time as possible. A scanning method is not limited to a sector scanning method, and instead, a linear scanning method and a convex scanning method may be employed.

A scan order shown in FIG. 2 is directed to performance of rate subtraction imaging. This scan order is formed to repeat two times of successive scans along each raster with a converged beam-like ultrasound pulse signal, with the scanned raster moved in a sector form. Specifically, the scanning is performed with the first and second scanning (1) and (2) assigned to the initial raster, the third and forth scanning (3) and (4) to the next raster, and so forth, and the 239-th and 240-th scanning (239) and (240) assigned to the last raster. In this case, the scanning is performed two times for each of the total of 120 rasters, that is, 240 times of scanning is performed.

Through this scanning technique, two echo signals responding to two times of transmission are acquired from each raster. In this embodiment, as described later, a difference signal is calculated by mutual subtraction carried out between the two echo signals present as being radio frequency (RF) signals. The rate subtraction imaging is based on the mutual subtraction between echo signals generated by a plurality of times of transmission of ultrasound signals successively done along each raster in response to each rated pulse.

This subtraction is able to cancel echo components (called as steady components), such as tissue echoes which are in a steady state and which cause no or almost no positional changes during a period of time between two times of transmission pulse applications. The microbubbles of a contrast agent are excited by the irradiation of ultrasound waves. Due to the fact that the excitation causes changes in the sizes of the microbubbles and/or their collapse phenomena, each echo signal component generated in response to each of the two times of transmission pulse applications differs in signal intensity and others from each other. As a result, mutually different components (referred to as a transient (or non-steady component) between two echo signals remain and are extracted as a difference signal.

In the present invention, as will be mentioned later, the contrast echo imaging is performed in a more optimum state by using the difference signal as well as an echo signal subjected to the subtraction.

Returning to FIG. 1, the output terminal of the adder of the ultrasound receiver 22 is connected to the subtraction circuit 23.

Figure 3:
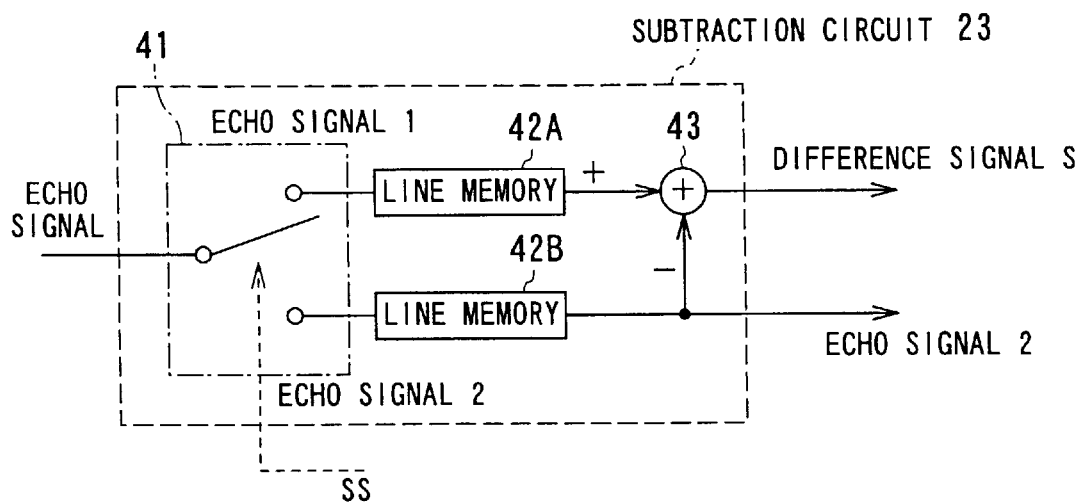
FIG. 3 is a block diagram showing a subtraction circuit according to the first embodiment.

The subtraction circuit 23, as shown in FIG. 3, is provided with a one-input and 2-outputs type of electric switch 41 capable of electrically switching over its output paths, two line memories 42A and 42B, and a single subtracter 43.

Hence, an echo signal outputted from the ultrasound receiver 22 is switched over by the electronic switch 41 in the order of scanning (i.e., the order of transmission and reception) (1) to (240), thereby producing the echo signal 1 or 2. This switchover is controlled by a switch signal SS supplied from the switchover control circuit 32. The order of transmission and reception, i.e., the scan order is odd numbers, such as (1), (3), (5), . . . , (239), the switch 41 is switched over to one output terminal, providing the echo signal 1. On the other hand, the scan order is even numbers, such as (2), (4), (6), . . . , (240), the switch 41 is switched over to the other output terminal, providing the echo signal 2.

The one switch output terminal, through which the echo signal 1 is produced, is coupled with a plus input terminal of the subtracter 43 via one line memory 42A. The other switch output terminal, through which the echo signal 2 is produced, is not only coupled with a minus input terminal of the subtracter 43 via the other line memory 42B but also taken out directly as one output of the subtraction circuit 23. The output of the subtraction circuit 23 is directly taken out as being the other output of the subtraction circuit 23. The outputs of the subtraction circuit 23 are therefore made up of a difference signal S (="echo signal 1"-"echo signal 2") depending on the outputs of the subtracter 43 and the echo signal 2. The subtracter 43 can be placed at the side of the line memory 42B, in which the echo signal 1 is used for the echo signal 2.

As shown in FIG. 1, the outputs of the foregoing subtraction circuit 23 is coupled with the data synthesizer 26 via the receiver 24 and B-mode DSC in turn. Each of the receiver 24, B-mode DSC 25, and data synthesizer 26 is composed of two systems correspondingly to the two-system output signals of the subtraction circuit 23, that is, the difference signal S and the echo signal 2. Those two systems are configured in functions to perform signal processing signal by signal in response to independent parameters and conditions. A user can specify such independent parameters and conditions by hand for each of the signals 2 and S by way of the keyboard or mouse of the operation panel 13. Instead of this, the parameters and conditions may be fixedly set as defaults signal by signal in advance.

Such independent signal processing is another characteristics of the present invention. That is, the processing is to optimize, in a mutually independent state, post-processing of the echo signal (steady signal component) from tissue and post-processing of the echo signal (transient signal component) from a contrast agent, before both of the signals are combined as images. The flows of the two types of independent signal processing are conceptually shown in FIG. 4. In this figure, the two types of processing are illustrated as if they are performed in parallel with different sets of hardware in each unit, but those two types of processing are carried out on a time-sharing basis in each unit, thus realizing functionally independent processing of each other.

The receiver 24 has hardware circuitry, though not shown, in which there is one system including a logarithm amplifier, envelope detector, and digital echo filter. In cases the apparatus is used for the harmonic imaging, the digital echo filter is given a characteristic of high-pass type of echo filter which enables only harmonic components of which frequency is for example double the transmission frequency of an ultrasound pulse signal. An echo signal acquired along each raster direction, to which the receiver 24 gives a reception directivity, is logarithm-amplified in digital amount, envelope-detected, and filtered through a desired frequency band. A resultant echo signal is then sent to the B-mode DSC 25.

The receiver 24 receives from the subtraction circuit 23 the difference signal S and the echo signal 2 in turn. In the receiver 24, each signal is subject to, under the same hardware circuitry and in an alternate and switchover manner on a time sharing basis, the foregoing signal processing (refer to 24A or 24B in FIG. 4) to which independently set parameters are assigned. This switchover is controlled responsively to the switchover command signal SR that receives from the switchover control circuit 32. Employing the time-sharing system can reduce the hardware circuitry down to one system, limiting the hardware in size. Alternatively, the time-sharing system may be replaced with the foregoing two-system hardware circuits prepared separately, in which both difference signal S and echo signal 2 are processed in parallel.

The processing 24A and 24B separately executed for both difference signal S and echo signal 2 in the receiver 24 will now be explained (refer to FIG. 4). In the receiver 24 in which a gain and a dynamic range of each signal are fundamentally determined, those parameters appropriate for intensities of both of the signals S and 2 are specified separately.

(As to processing 24A)

The signal processing for the echo signal 2, which is based on independently set parameters, is directed to depicting tissue tomographic images in optimum image quality. Therefore, various kinds of processing that have been performed in the conventional diagnostic ultrasound apparatus are applied to the processing 24A. For example, for depicting the liver, the cut-off frequency and bandwidth (parameters) of the digital echo filter based on the receiver processing are finely adjusted depth by depth for filtering so that a speckle pattern of the liver is maintained uniformly even when the depth is changed.

(As to processing 24B)

According to inventor's knowledge, the difference signal S is lower by an amount of about 20 to 30 dB in average intensity than the echo signal 2. Thus, the gain (i.e., one parameter) for the difference signal S in the receiver 24 is set to an amount higher than that for the echo signal 2. Further, for processing echoes emanated from the contrast agent, the bandwidth of the probe has priority over the uniformity of the speckle pattern. Namely, the bandwidth (i.e., a parameter) of the echo filter is determined so that intensities of echoes from the microbubbles are detected as being larger amounts. Further, in the processing 24B for the difference signal S, there are some cases that an echo filter for harmonic imaging is used.

Signal components of both echo signal 2 and difference signal S processed by the receiver 24 are freely selected and combined to each other. For example, 1) both echo signal 2 and difference signal S are processed at the frequency corresponding to the fundamental component of transmission ultrasound waves, 2) the echo signal 2 is processed at the frequency corresponding to the fundamental component of transmission ultrasound waves, whilst the difference signal S is processed at the frequency corresponding to a harmonic component of the transmission ultrasound waves, and 3) both echo signal 2 and difference signal S are processed at the frequency corresponding to a harmonic component of transmission ultrasound waves. The above second and third processing techniques involve harmonic imaging. Depending on any combination of the frequencies to be used, the parameters (such as gain and/or cut-off frequency) of the digital echo filters are adjusted appropriately. The foregoing two types of processing 24A and 24B are performed independently of each other according to combined types of the signals.

The difference signal S and echo signal 2, both of which have been processed by the receiver 24, are sent to the B-mode DSC (Digital Scan Converter) 25, respectively.

The DSC 25 converts each input signal from its raster signal trains based on the ultrasound scanning to that based on a video format, and then sends it to the data synthesizer 26. In this DSC 25, both difference signal S and echo signal 2 are alternately switched over therebetween on a time-sharing basis and scan-converted by the same hardware circuit thereof by using scan parameters separately set to each signal (refer to 25A and 25B in FIG. 5). This switchover is controlled responsively to a switchover command signal SD sent out from the switch control circuit 32. Like the above, the parallel processing is also available in this converter.

Processing 25A and 25B, which are called post-processing (PP), executed separately from each other for both of the difference signal S and echo signal 2 in the B-mode DSC 25 will now be explained (refer to FIG. 4).

(As to processing 25A)

In the signal processing 25A for the echo signal 2, intensity values are differentiated (intensity differentiation) in the depth direction in a tomographic image of tissue, according to its necessity, as additional processing to the scan conversion that is a basic operation. The differentiation emphasizes the boundary of tissue. Particularly, such a boundary emphasis is suitable for imaging the heart. For imaging the abdomen that has less motion, frame correlation processing is additionally executed in this processing 25A. This correlation processing is a technique to overlay a several percentages of intensity on past frame images onto the current frame image, thus providing images on which an afterimage feeling lingers and reducing flickers of noise.

(As to processing 25B)

The processing for the difference signal S in the B-mode DSC 25 is mainly the scan conversion that is the fundamental operation of the DSC. That is, the intensity differentiation and/or frame correlation processing, which are additionally carried out in the above processing 25A, will not be carried out in this processing 25B. Therefore, it is avoided that transient behaviors of microbubbles go out of sight due to such additional processing.

Each of the difference signal S and echo signal 2 scan-converted by the B-mode DSC 25 is sent to the data synthesizer 26.

The data synthesizer 26 synthesizes two frames of B-mode image data, which are the received difference signal S and echo signal 2, into one frame of image in which the original two frames are located side by side or superposed one on the other. Additionally, the data synthesizer 26 overlays on the one frame of image such data as characters and scales (graphic data) sent from the data generator 31.

This synthesis is another characteristic of the present invention, in which a tomographic image of tissue composed of the steady signal component and a tomographic image of the contrast agent composed of the transient signal component are displayed at the same time.

As display modes of both tomographic images, there are prepared a plurality of modes described later. Which display mode is selected is decided by a selection signal SP sent from the controller 30. The selection signal SP corresponds to an operator's command. FIGS. 5, 8, 9, and 10 shows examples of a variety of display modes, and those will be detailed later.

In cases a display mode specified by the selection signal SP requires a color-coded tomographic image, a color coding circuit 27 contained in the data synthesizer 26 responds pixel by pixel to code various colors on image data based on both difference signal S and echo signal 2. Image data of pixels that do not experience color-coding are dealt with gray-scale image data.

Figure 4:
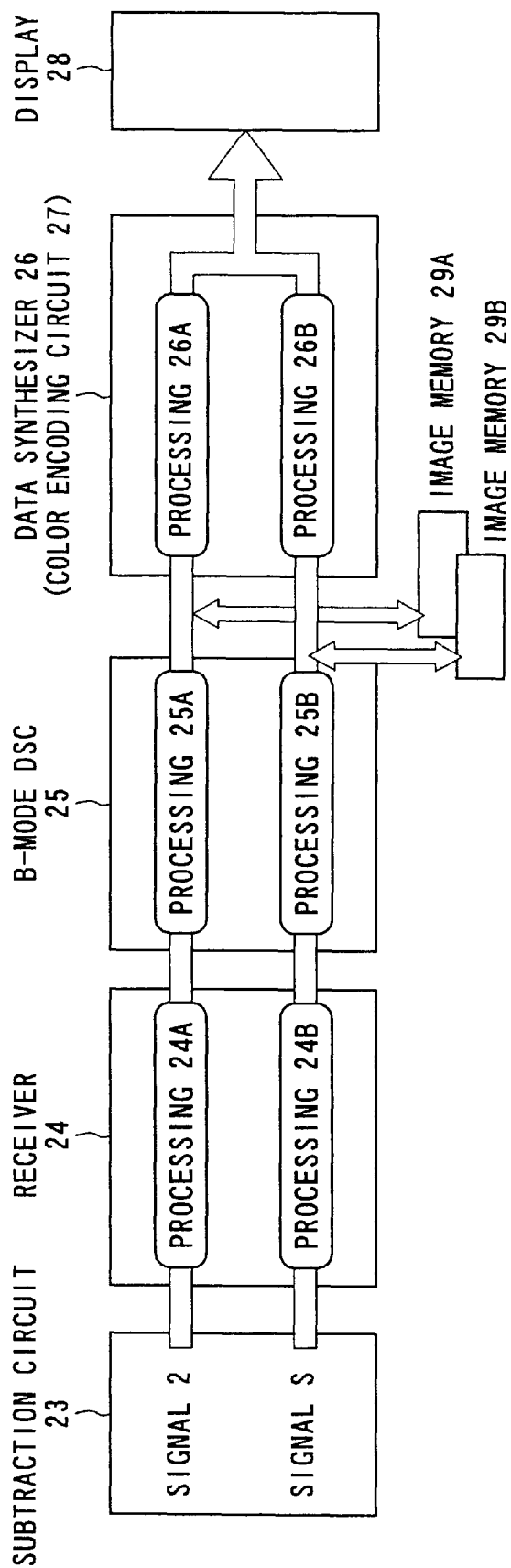
FIG. 4 is a pictorially written functional block diagram for processing an echo signal and a difference signal independently of each other.

In this synthesis, the same hardware circuit of the data synthesizer 26 operates on a time-sharing basis under parameters specified for each of the difference signal S and echo signal 2, so that both signals S and 2 are alternately switched over from one side to the other to receive signal processing 26A or 26B (refer to FIG. 4). The signal processing includes interpolation processing. The switchover is controlled by a switchover command signal SZ sent from the switchover control circuit 32. Instead of the time-sharing processing, parallel processing may be used, like the above.

(As to processing 26A)

The signal processing 26A of the echo signal 2 includes interpolation processing. By the interpolation processing performed using signals produced by rearranging intensity signals along the rasters and scan-converting those in the DSC 25, each location to be interpolated on an image is interpolated, location by location, through collection of intensity signals residing over as far range as possible. This produces image data of which bit map information shows an organ's smoothed speckle pattern.

(As to processing 26B)

Although the signal processing 26B of the difference signal S includes interpolation processing as well, the contents of the interpolation processing differ. Since an echo signal reflected from microbubbles of the contrast agent is a transient signal, there may frequently occur the case that a difference signal of intensity is large is obtained for a certain raster, but a difference signal will no longer occur for an adjacent raster to the certain raster due to collapse of the microbubbles on the adjacent raster. If the interpolation technique in the processing 26A is applied to this case, the interpolation becomes unreasonable on account of using totally random intensity information. That is, in this processing 26B, intensity information obtained from a distant region hardly makes sense. Thus, interpolation such as linear interpolation is carried out location by location by using intensity information acquired from only a neighboring region.

The image data thus synthesized are finally sent to the display 28. In the display 28, the image data are converted into analogue signals by a D/A converter incorporated therein, before being displayed on the display screen of for example a TV monitor as a tomographic image representing the structure of an object's tissue. A desired region on this displayed tomographic image is given colors pixel by pixel.

Each of the image memories 29A and 29B is coupled with the B-mode DSC 25 and has a memory element into which processed signals in the DSC 25 (i.e., raster signal trains on the ultrasound scanning and/or raster signal trains on the video format) and a read/write control circuit for the memory element. The foregoing processed signals of each of the difference signal S and echo signal 2 are stored separately into each of the image memories 29A and 29B. Specifically, the storage of signals processed from the difference signal S is assigned to one image memory 29A, while the storage of signals processed from the echo signal 2 is assigned to the other image memory 29B.

The image signals thus memorized into the image memories 29A and 29B can be read frame by frame during scanning (i.e., diagnosis on the spot) or after the scanning and utilized. For utilizing this, the signals read from the image memories 29A and 29B are sent to the data synthesizer 26 via the B-mode DSC 25, wherein the image synthesis mode is altered and adjusted to an appropriate one in cases the signals are displayed as images. The data of the images are sent to the display 29 for display.

The controller 30, configured into a computer having a CPU and memories, controls the entire operations of this apparatus on the basis of the previously programmed procedures. This control operation includes transmission control for the transmitter 21 (such as transmission timing and transmission delays), reception control for the receiver 22 (such as reception delays), command to the data generator 31 to produce displayed data such as character information and scales, output of the selection signal SP for a display mode specified by an operator using the operation panel 13, output of the control signal SC for signal processing parameters specified by an operator using the operation panel 13, control for driving the switchover control circuit 32, and control of operation timing for other constituents.

The data generator 31 responds to a command to produce display data, the command being sent from the controller 30. This response causes the data generator 31 to produce graphic data of a specified ROI (region of interest) and character data such as annotations for sending those data to the data synthesizer 26. Further, the switchover control circuit 32, which responds to an operation command from the controller 30, switches over the signal processing in the receiver 24, B-mode DSC 25, and data synthesizer 26 on a time-sharing basis to each of the echo signal 2 and the difference signal S. This switchover control provides independently performed processing to each of the echo signal 2 and the difference signal S, as shown in FIG. 4.

Referring to FIGS. 5 to 10, first to fourth display modes on each of which synthesis is done in the data synthesizer 26 will now be explained. An operator can choose any of the display modes. Incidentally, although not shown, the diagnostic ultrasound apparatus has another function of solely displaying B-mode tomographic images based on the echo signal 2 (or echo signal 1).

(First display mode)

Figure 5:
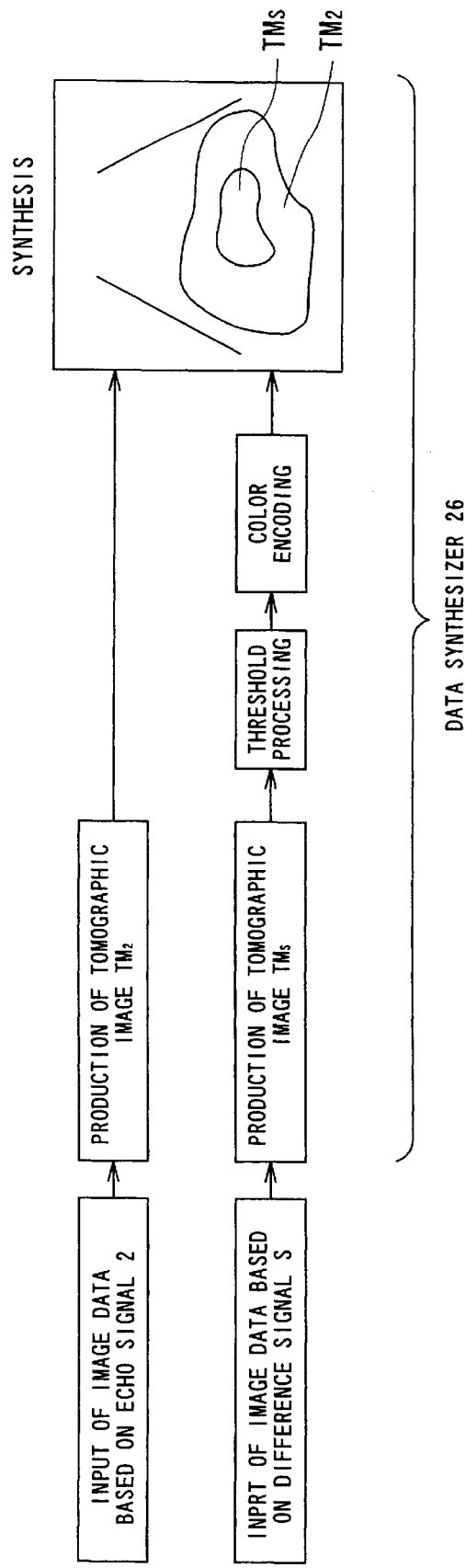
FIG. 5 is an outlined flowchart explaining synthetic processing of images according to a first display mode.
Figure 6:
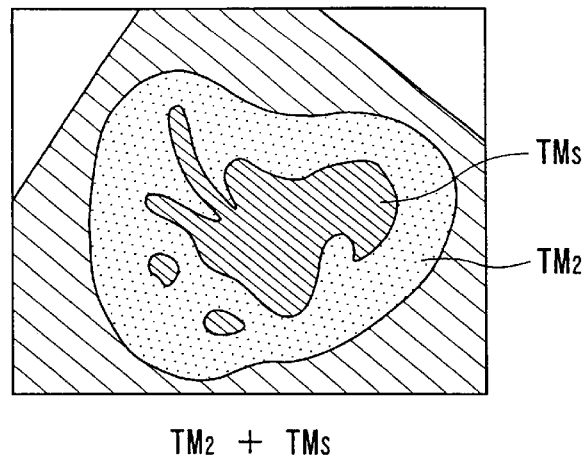
FIG. 6 shows a monitor screen exemplifying the first display mode.

FIG. 5 shows an outlined of data synthesis processing according to the first display mode and FIG. 6 exemplifies the display.

As shown in FIG. 5, a tomographic image $TM_2$ based on the echo signal 2 is produced as a B-mode image (i.e., gray-scale image) in the similar way to conventional B-mode images. For a tomographic image $TM_S$ based on the difference signal S, only pixels whose intensity equals a predetermined threshold or is over the threshold are extracted, and color-coded in, for example, red or blue, thereby being produced as a color-mapped image. Then, the image data of the tomographic image $TM_S$ based on the difference signal S are superposed on the image data of the tomographic image $TM_2$ based on the echo signal 2. This superposition is made such that, at locations where the tomographic image $TM_S$ are present, pixels of the tomographic image $TM_S$ have priority over those of the tomographic image $TM_2$. In contrast, at the remaining locations where the tomographic image $TM_S$ are absent, pixels of the tomographic image $TM_2$ are chosen, so that the tomographic images are superposed.

As a result, as shown in FIG. 6, with one tomographic image $TM_2$ used as a background image, the other tomographic image $TM_S$ are overlaid thereon, and the superposed image is displayed on the display 28. Pixels of the tomographic image $TM_S$ based on the difference signal S are set to be clear if the pixels are below the predetermined threshold. Therefore, in such a region whose pixels are clear, pixels of the background tomographic image $TM_2$ are represented. According to the tomographic image $TM_S$, a region of pixels at each of which the difference signal S, i.e., the transient echo component exists will be displayed distinctly, being excellent in observing the outline of the region, though the surrounding area of the region is poorly displayed in that subtle changes in intensity in the surrounding area will not be represented.

(Second display mode)

Figure 7:
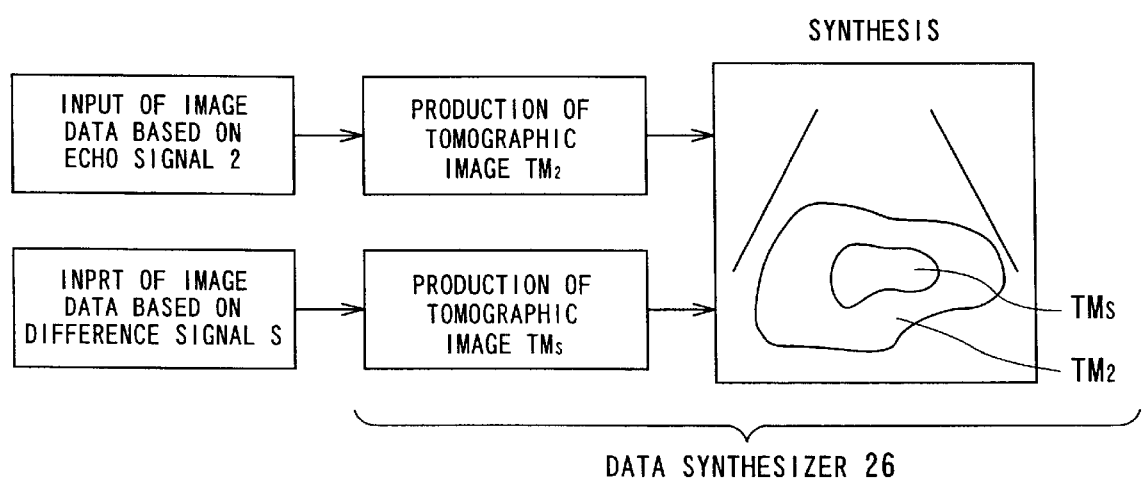
FIG. 7 is an outlined flowchart explaining synthetic processing of images according to a second display mode.
Figure 8:
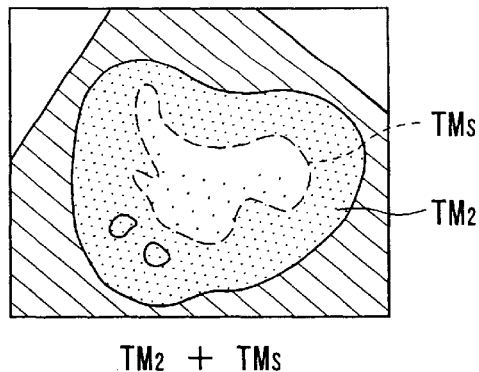
FIG. 8 shows a monitor screen exemplifying the second display mode.

FIG. 7 shows an outlined of data synthesis processing according to the second display mode and FIG. 8 exemplifies the display.

As shown in FIG. 7, the tomographic image $TM_2$ based on the echo signal 2 is produced as a B-mode image (gray-scale image). For the tomographic image $TM_S$ based on the difference signal S, the pixels are color-coded in, for example, red or blue, being produced as a color-mapped image. After the production, the image data of tomographic image $TM_S$ based on the difference signal S are superposed on those of tomographic image $TM_2$ based on the echo signal 2. In this superposition, each pixel of one topographic image $TM_S$ is added in a pixel value (intensity) to that of each pixel the other tomographic image $TM_2$, thus providing a superposed image.

As a result, as shown in FIG. 8, with one tomographic image $TM_2$ used as a background image, the other tomographic image $TM_S$ are overlaid thereon, and the superposed image is displayed on the display 28. The superposed image is entirely influenced in intensity by the intensity of the echo signal from tissue, but the tomographic image $TM_2$ based on the echo signal 2 also includes an intensity-enhanced component by the contrast agent. Thus, visibility for a colored region (intensity region based on the difference signal S) is raised. Additionally, making an intensity range to the echo signal 2 narrower (for example, an intensity range of 256 gradations are reallocated to that of 40 gradations) enables a more distinct observation of the difference signal S, while still maintaining a higher depiction performance of tissue.

According to inventor's study, it has been confirmed that the foregoing tomographic image $TM_S$ based on the difference signal S still provides relatively higher visibility even when the topographic image $TM_S$ is displayed in gray scales, not colors, because of its higher intensities of the image.

(Modification of second display mode)

The foregoing second display mode can be reduced to practice, as follows, by recalculating intensities to be displayed.

Figure 9:
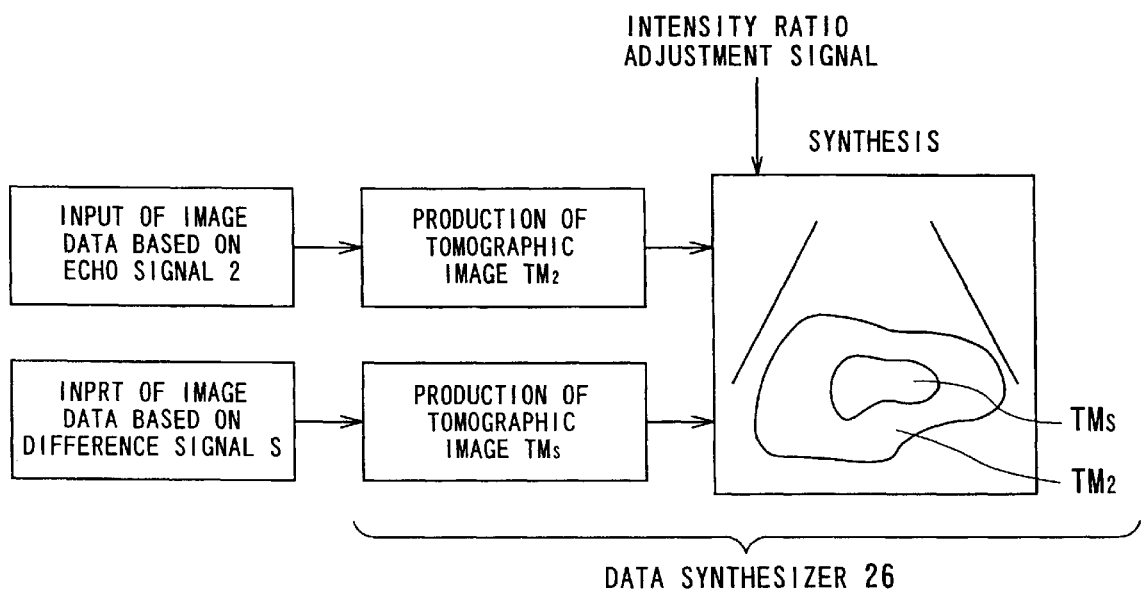
FIG. 9 outlines a flowchart explaining another synthetic processing of images according to the second display mode.

The present modification uses an intensity ratio a ($0 \leq a \leq 1$) of the tomographic image $TM_S$ based on the difference signal S. An operator can operate the operation panel 13 to specify the intensity ratio a to be a desired amount. As shown in FIG. 9, the desired amount of the intensity ratio a is sent as an intensity ratio adjustment signal Sa to the data synthesizer 26 through the controller 30. Thus, the data synthesizer 26 recalculates intensities on the basis of the following formula.

That is, in the data synthesizer 26, the image data of both tomographic images $TM_S$ and $TM_2$ are synthesized one on the other and an intensity B at each displayed pixel on the synthesized image is recalculated on the following formula:

$$B = a \cdot TM_S + (1-a) \cdot TM_2$$

The thus-synthesized image data of which intensities has been recalculated are sent to the display 28 for display thereof.

In the case of the intensity ratio a=1, the synthesized image is displayed so that the components of the tomographic image $TM_S$ based on the difference signal S occupy 100 percents of the image. By contrast, in the case of the intensity ratio a=0, the synthesized image is displayed so that the components of the tomographic image $TM_2$ based on the echo signal 2 occupy 100 percents of the image. Further, in cases the intensity ratio a is 0<a<1, the display is performed in such a manner that the components of both tomographic images are mixed with each other depending on the ratio.

During scanning performed in real time or replay of image data read from the image memories 29A and 29B, an operator can freely adjust a mixing ratio between both of the topographic images $TM_S$ and $TM_2$ by hand through the operation panel 13. Therefore, superposed images between the tomographic images $TM_S$ and $TM_2$ can be obtained during the diagnosis, as one of the difference signal S or echo signal 2 is raised or lowered in intensity. Scanned conditions can therefore be confirmed by observation with ease during the diagnosis.

Incidentally, adjusting the intensity ratio a is not limited to the configuration of being specified by hand through the operation panel during scanning, but can be set to an appropriate default value in advance. It is also possible that the default value is altered scan by scan beforehand.

(Third display mode)

Figure 10:
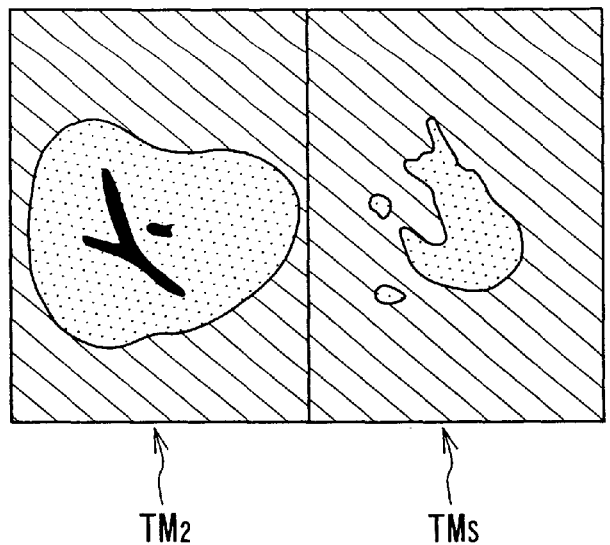
FIG. 10 shows a monitor screen exemplifying the third display mode.

FIG. 10 exemplifies the display according to the third display mode.

As shown in FIG. 10, both of the tomographic image $TM_2$ based on the echo signal 2 and the tomographic image $TM_S$ based on the difference signal S are generated as B-mode images (gray-scale images) which are like the conventional. These topographic images $TM_2$ and $TM_S$ are displayed side by side on the screen.

Where both tomographic images are superposed one on the other like the first and second display modes, locations at which the contrast agent is present can be determined with ease. However, in such a superposition manner, the depiction performance of a speckle pattern obtained by the B-mode is not completely held. Hence, displaying both tomographic images $TM_2$ and $TM_S$ side by side in this way makes it possible to observe a sensitive speckle pattern with a steady manner.

(Fourth display mode)

Figure 11:
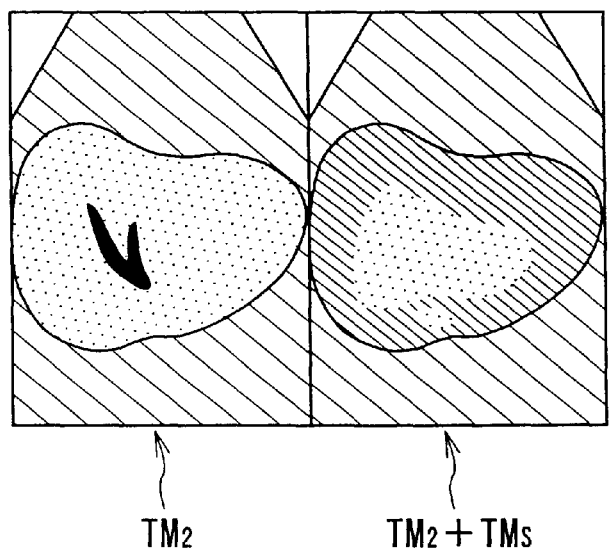
FIG. 11 shows a monitor screen exemplifying the fourth display mode.

FIG. 11 exemplifies the display according to the fourth display mode.

The display mode shown in FIG. 11, which is modified from the third display mode (refer to FIG. 10), is realized by replacing, as to the tomographic image $TM_S$ based on the difference signal S, the image shown in FIG. 9 with one shown in FIG. 2 (second display mode). Specifically, as shown side by side in FIG. 11, at the left on the screen of the display 28 is displayed the tomographic image $TM_2$ based on the echo signal 2, while at the right thereof is displayed a superposed image "$TM_2+TM_S$" based on both signals 2 and S generated like FIG. 8. In the image "$TM_2+TM_S$," a range of intensities of the image $TM_2$ based on the echo signal 2 are narrowed largely.

As a result, the outlined shape of tissue can be observed in a comparison manner between two conditions in which the topographic image $TM_S$ is overlaid and not overlaid. A detailed image of the tissue can be obtained as the tomographic image $TM_2$, thus image information being supplied in detail concurrently.

Other modifications can be provided as well. For displaying two types of tomographic images in parallel as the above, the size of each image or a ratio between the sizes thereof may be changed appropriately. As another display mode other than the above described, a mode in which only a B-mode tomographic image based on the echo signal 2 is displayed like the conventional can be adopted.

The operation and advantages of the present embodiment will now be described.

It is now supposed that, as the ultrasound contrast agent of which main constituent is microbubbles is persistently injected into an object, the contrast agent inflowing into for example the cardiac muscle, that is, a perfusion of tissue blood, is examined on the contrast echo technique.

Responsively to transmission of ultrasound pulse signals, ultrasound echoes scattered by tissue and/or the contrast agent within the object are received by the probe 12, and converted into electric echo signals by its vibrators. The echo signals are then sent from the probe 12 to the ultrasound receiver 22 channel by channel, in which the echo signals for all the channels are beam-focused, forming a converged echo signal, as described before. The converged echo signal is then sent to the subtraction circuit 23. This echo signal is generated for each scan.

The switchover control circuit 32 turns on or off the switchover signal SS, so that, in response to those switchovers, the output destination from the electric switch 41 of the subtraction circuit 23 is selectively changed to one line memory 42A or to the other line memory 42B according to a scan order of (1), (2), ..., (240). In other words, as shown in FIG. 2, an echo signal 1 is temporarily stored in the one line memory 42A when the odd number-th scan is performed, while an echo signal 2 is temporarily stored in the other line memory 42B when the even number-th scan is performed.

In the subtraction circuit 23, the temporarily stored echo signals 1 and 2 are subject to subtraction conducted by the subtracter 23, both of a difference signal S ("echo signal 1"–"echo signal 2") and the echo signal 2 (or echo signal 1) which has experienced no calculation being provided.

By each of the receiver 24, B-mode DSC 25, and data synthesizer 26, the echo signal 2 and difference signal S are then subjected to signal processing of which parameters and conditions are separately specified as functionally shown in FIG. 4. The signal processing is performed by the switchover control on a time-sharing basis in compliance with the command signals SR, SD, and SZ given by the switch control circuit 32. To be specific, the echo signal 2 is subject to receiver processing 24A in the receiver 24, then to scan conversion processing 25A in the DSC 25, and then to interpolation processing 26A in the data synthesizer 26. On the other hand, the difference signal S is subject to receiver processing 24B in the receiver 24, then to scan conversion processing 25B in the DSC 25, and then to interpolation processing 26B in the data synthesizer 26.

Then, in the data synthesizer 26, a final superposed tomographic image is produced in response to a display mode commanded by an operator through a selection signal SP. Depending on which display mode is commanded, pixels to be necessary are encoded in colors, then sent to the display 28. When any display mode characterized by the present invention is selected and commanded from all the display modes, a tomographic image $TM_2$ based on the echo signal 2 and a tomographic image $TM_S$ based on the difference signal S are displayed together.

Figure 12A:
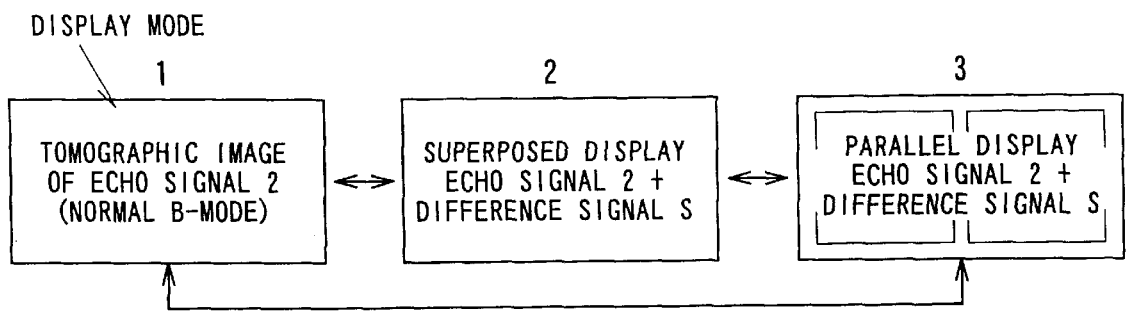
FIG. 12A shows successive switchovers of display modes.
Figure 12B:
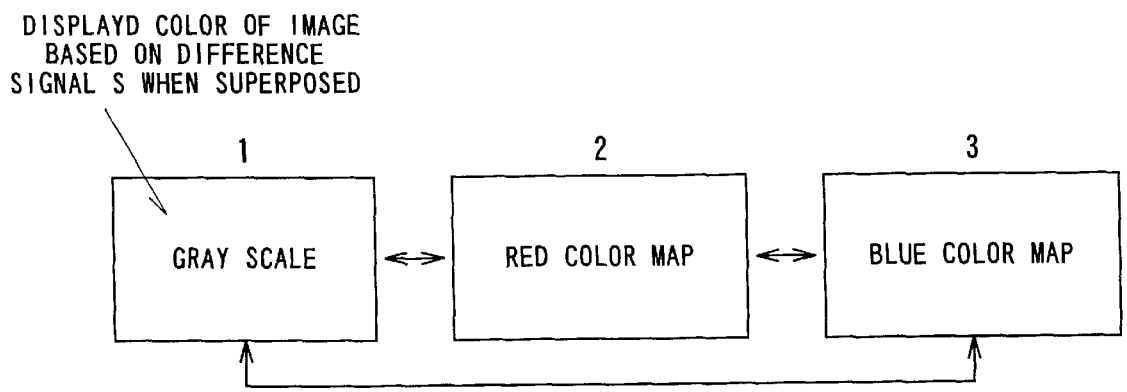
FIG. 12B shows successive switchovers of displayed colors.

Once a certain display mode is selected and the display is done on the display mode, the diagnosis can be kept with the display mode. Alternatively, the operator can operates, at one touch, the operation panel 13 at hand, in such a manner that a plurality of types of images are displayed in turn for diagnosis, as shown in FIGS. 12A and 12B, as the display mode and/or colors are appropriately selected and changed. For example, as shown in FIG. 12A, the display mode can be switched over in an appropriate order and at appropriate timing among the sole display of a B-mode tomographic image based on the echo signal 2, the superposed display of the tomographic images based on the echo signal 2 and difference signal S (refer to FIGS. 6 and 8), and the superposed display of the tomographic images based on the echo signal 2 and difference signal S (refer to FIGS. 10 and 11). In the case of displayed colors, as shown in FIG. 12B, gray-scale display, red color mapping display, and blue color mapping display can be switched over in an appropriate order and at appropriate timing. As to the types of colors, colors other than red and blue can be adopted.

Therefore, in the present embodiment, the difference signal S is calculated from two echo signals acquired along each raster according to the rate subtraction imaging (RSI). This rate subtraction imaging uses two times of successive transmission of an ultrasound beam along each raster. However, microbubbles of the contrast agent that are present on each raster are not completely collapsed by one time of transmission. It is true that microbubbles remain to some extent, without being collapsed entirely. Hence, an echo signal can be detected by each of the two times of transmission, resulting in that a transient echo component inherent to the contrast agent is separated with certainty from a steady echo component depending on tissue.

In particular, since the rate subtraction imaging is employed, there are various advantages of superior spatial resolution, less speckles, higher realtime performance (temporal resolution), and others, compared to subtraction between frames, that is, the inter-frame subtraction technique. When it is not necessary to strength the realtime performance, there is the advantage that an intermittent transmission technique can be used together.

Further, the rate subtraction, which is in charge of the subtraction circuit 23, is performed without fail at the signal stage before the receiver 24. That is, the rate subtraction is performed at the stage of radio frequency signals that are previous to intensity image signals detected by the receiver 24. Once being converted into intensity data, the rate subtraction is not effective (does not make sense), so the subtraction is carried out in the radio frequencies.

As to the two signals separated by the rate subtraction, post-signal processing is individually performed using parameters and conditions (frame rates, after-image of frame, spatial intensity differentiation, and others) determined inherently with consideration of characteristics and others to ultrasound waves irradiated onto to a contrast agent and tissue. Each of the echo and difference signals is therefore independently processed by the post processing in an optimum state to each signal without losing echo information given to the echo signal. Each of the detected echo signal and the calculated difference signal shows the maximum visibility when being displayed as an image.

The echo and difference signals are individually produced into image data of the tomographic images, separately from each other. Both tomographic images are then combined to each other into one image for display. The displayed image always includes information in relation to a transient echo component from the contrast agent and information in relation to a steady echo component mainly from tissue. Moreover, each of the image information on the transient echo component and the image information on the steady echo component is produced after the post-signal processing conducted separately from each other, thus an optimized contrast agent echo image and an optimized tissue echo image being displayed.

Accordingly, performing the contrast echo imaging on the rate subtraction imaging enables the contrast agent, i.e., minute blood flows in tissue to have a higher depiction performance by nature. Unlike the conventional technique that a tissue harmonic component (tissue echo) generated from the organic tissue makes it difficult to observe minute blood flows, a raised visibility performance for the minute blood flows can be obtained at any time. Compared to the conventional, a diagnostic capability on the contrast echo imaging can therefore be improved greatly and more stable diagnosis can be obtained.

In observing dynamics of minute blood flows of tissue on the contrast echo imaging, the morphological image information of the tissue is displayed together. Thus, it is easier for an observer to spatially understand a spread of positions of minute blood flows within an entire organ with ease and without fail. This brings about excellency in convenience of use and further increases a diagnostic performance, in addition to the foregoing higher visibility. Furthermore, an operator is able to easily switch over the screens and obtain the most easy-to-see image or a desired image on the spot, with burden on the operation and work lessened.

Further, in the contrast echo imaging on the rate subtraction imaging, the echo signal 2 and difference signal S are produced together, and signal-processed separately. It is therefore possible that the extracted contrast agent echo image is displayed in a display mode and colors specified by the foregoing various synthesis methods. An observer can appropriately select a desired display mode as well as can switch over a plurality of display modes for observation. In diagnosing minute blood flows, observation can be done from various angles, such that the same location is scanned and displayed through a plurality of types of display modes or colors. This enables the same location to be confirmed by each image, thus increasing reliability in diagnosis.

In the present embodiment, both foregoing echo images can be displayed concurrently in real time during scanning of an object.

By contrast, there are the image memories 29A and 29B each assigned to the echo signal 2 and difference signal S, which will lead to the characteristic that the images are always divided and preserved signal by signal. This permits the image to be post-processed freely after a scan. For example, image data are read out from the image memories 29A and 29B, respectively, before a tissue echo image and a contrast agent echo image, which are produced in the similar manner to the above, can be displayed in a superposed state or parallel state. Even either one image can be displayed solely. In such display, the display mode can be switched over an appropriate timing. This way of display carried out after scan still provides the foregoing advantages resulting from the separate processing for both echo signals and simultaneous display of two tomographic images produced from both of the echo signals.

Since the ultrasound imaging using the contrast echo technique of the present embodiment is based on the rate subtraction imaging, the following advantages are given when being compared to the phase pulse addition technique.

First, the phase pulse addition technique requires all the second harmonic components to be extracted. Thus a steady harmonic component from tissue is also included in the detected component (i.e., extracted). In contrast, in the rate subtraction imaging, the steady component is canceled, only a transient echo component being extracted. That is, the harmonic component from tissue is not extracted.

Second, the phase pulse addition technique needs a probe to have a broad frequency bandwidth in sensitivity, because the technique is directed to depiction of second harmonic components. For example, if a transmission frequency is 3 MHz, its reception frequency is 6 MHz, requiring a probe sensitivity to have a band of at least 3 to 6 MHz. The higher the frequency band, the more the loss in the transmission of ultrasound waves, thereby lowering sensitivity. By contrast, when the rate subtraction technique is used on condition that a transmission frequency is 3 MHz, for example, a difference in signal intensities is detected at the same frequency, 3 MHz. It is not therefore necessary to worry about lowered sensitivity.

(Second Embodiment)

Figure 13:
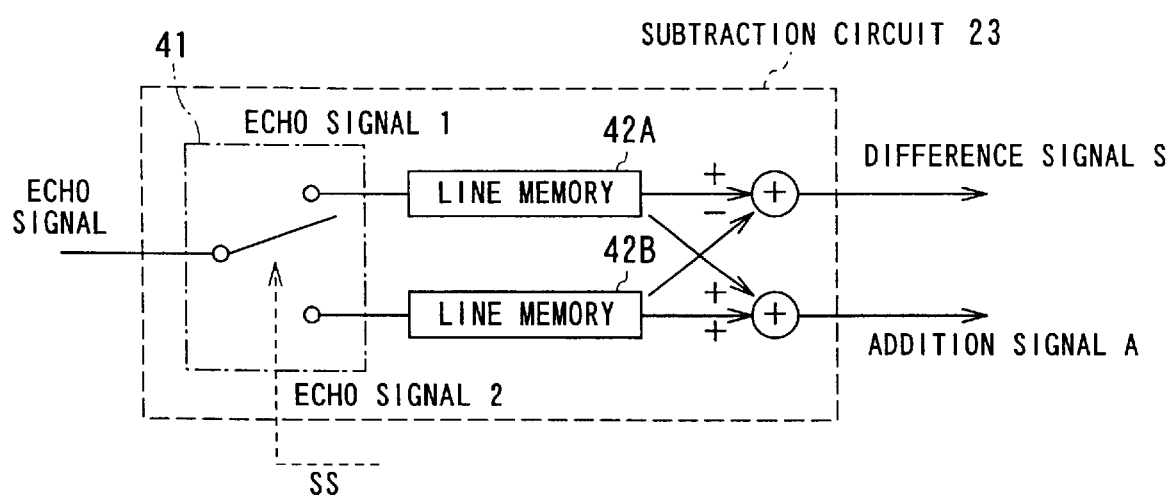
FIG. 13 is the block diagram of a subtraction circuit according to a second embodiment.

Referring to FIG. 13, a diagnostic ultrasound apparatus according to the second embodiment will now be described.

The present diagnostic ultrasound apparatus functions in the similar ways to that in the first embodiment, but differs from it in that the subtraction circuit 23 is configured as shown in FIG. 13. The remaining configurations are identical to those in the first embodiment.

As shown in FIG. 13, the subtraction circuit 23 is provided with the electric switch 41, the line memories 42A and 42B, the subtracter, and an adder 44. Compared to the configuration of FIG. 3, the adder 44 is newly installed. The adder 44 mutually adds signals read from the line memories 42A and 42B so as to produce an added signal A ="echo signal 1"+"echo signal 2." The produced signal A is outputted instead of the foregoing echo signal 2.

In other words, each of the difference signal S and added signal A is sent from the subtraction circuit 23 to its succeeding elements, in turn, consisting of the receiver 24, B-mode DSC 25, and data synthesizer 26. This makes it possible to perform the foregoing independent post-signal processing with each of the difference signal S and the added signal A, providing a superposed image of those signals.

Therefore, in addition to the foregoing difference signal S, the added signal A is produced by averaging the echo signals 1 and 2. The averaging causes a transient echo component to lessen in the added signal A, emphasizing a steady echo component from tissue. As a result, a tissue echo image displayed together with a contrast agent echo image is further improved in depiction performance.

All the independent post-signal processing, production of display modes and display colors, and switchover control of those display modes and display colors, which have been explained in the first embodiment, can be applied to the second embodiment, providing the similar operations and advantages.

(Third Embodiment)

Figures 14A, 14B:
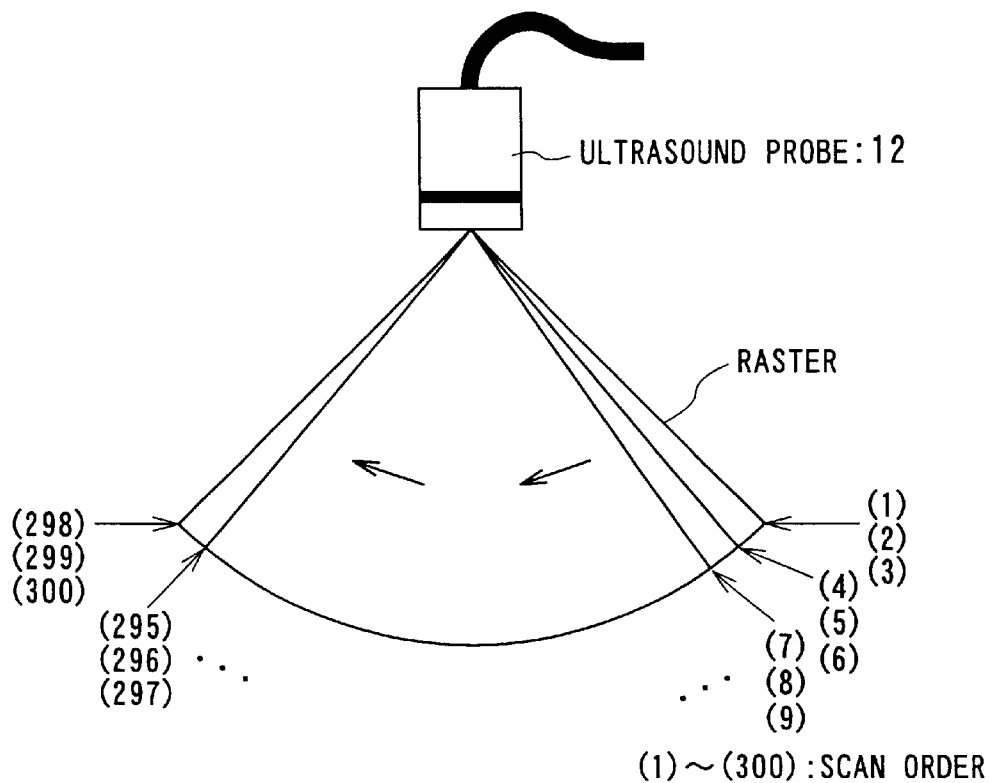
FIG. 14A explains a scan order according to a third embodiment.
FIG. 14B explains a scan order according to a variation of the third embodiment.

Referring to FIG. 14A, a diagnostic ultrasound apparatus according to a third embodiment of the present invention will now be explained.

The diagnostic ultrasound apparatus is characterized by the number of scan times (the number of transmission and reception times) per one raster. That is, though the number of scan times is set to two times in the foregoing embodiments, it can be set to three or more times.

FIG. 14A shows one example, in which the number of scan times is assigned to three. When referring to this example, of all rasters of 100 pieces, the scan orders (1), (2) and (3) are assigned to the first raster, the scan orders (4), (5) and (6) are assigned to the adjacent raster, and so on. To the final raster, the scan orders (298), (299) and (300) are assigned. For each raster, a difference signal S is calculated from two signals depending on the first and third scans. The foregoing echo signal, which is paired with this difference signal S, is assigned to one of such two echo signals or an added signal produced by averaging, like the second embodiment.

In this rate subtraction imaging, the two echo signals on the first and third scan are used for subtraction, so that an interval of time between the two echo signals becomes longer, and/or, the second transmission intervenes between the two times of transmission. The microbubbles of the contrast agent shows large changes in behavior, which causes the difference signal S to be large in intensity. Namely, a transient echo component inherent to the contrast agent increases in intensity, with the result that a depiction performance for the contrast agent echo image is improved. However, in cases the interval of time is too large to ignore motions of an internal organ, it is assumed that echoes from the internal organ may be mixed with the difference signal S. It is therefore the most suitable that the number of scan times (i.e., the number of transmission/reception times) per raster is set to two or three times.

As a modification of the foregoing imaging, a technique shown in FIG. 14B can be provided. This modification uses the second scan among the three times of scans per each raster shown in FIG. 14A as another type of transmission B to excite microbubbles. Differently from the first and third transmission directed to imaging, the transmission B is dedicated to excitation of physical states of microbubbles. This excitation is done to make it large differences of natures (intensity and others) between the echo signal 1 acquired from the first scan (transmission 1) and the echo signal 2 acquired from the third scan (transmission 2). Namely, a transient echo component comes into a more noticeable state. To realize this, an ultrasound signal usable for the other transmission B is formed into a signal wave that is relatively lower in frequency, lager in the number of continues waves, and relatively larger in amplitude. Intervening the other transmission B further increases the depiction performance of the foregoing contrast agent echo image.

The foregoing various embodiments have been described as mere examples and are not intended to limit the scope of the present invention. The scope of the present invention should be understood based on the appended claims, and various other modes could be reduced into practice without departing from the scope of the present invention.

As described above, the diagnostic ultrasound apparatus and the ultrasound diagnosis method performs contrast echo imaging under which an ultrasound contrast agent of which essential constituent is microbubbles is injected into an object. A transient echo component inherent to the contrast agent is extracted from a tissue echo component. A signal based on the extracted echo component and an original echo signal are processed separately, and then produced into separate tomographic images, with a combined image produced from the tomographic images. This provides a contrast agent echo image and a tissue echo image at the same time. Both echo images are produced in their optimum states, respectively, so that depiction capability for both images are kept excellent, thus excluding the state that one image is obliged to be lowered in depiction capability because the other image is given priority of depiction. Concurrently, a higher visibility of tissue blood flows is ensured. Compared to the conventional technique, a diagnostic performance on the contrast echo imaging can be upgraded remarkably, thus providing higher reliability for diagnosis.

Therefore, both of information about blood flow dynamics of blood vessels and information about dynamics of blood behavior at a level of organ tissue detected as perfusion can be quantified with high precision and with high fineness. It is therefore possible to provide detailed information in relation to screening diagnosis with a steady manner.

What we claim is:

1. A diagnostic ultrasound apparatus for obtaining an image of a region to be scanned by scanning an object with a beam-shaped ultrasound signal produced as a radio frequency signal, an ultrasound contrast agent being injected into the object, the apparatus comprising:
   a scanning unit configured to transmit the ultrasound signal a plurality of times in each scanning direction along the region to be scanned and receiving an echo signal generated from the object in response to each time of transmission of the ultrasound signal in each scanning direction;
   a subtracting unit configured to obtain a difference signal by performing subtraction between first and second echo signals each still being the radio frequency signal, the first and second echo signals being from the plurality of echo signals received in response to the transmission of the ultrasound signal in the same scanning direction;
   a producing unit configured to produce the difference signal into a first tomographic imageby a rate subtraction imaging technique using first processing conditions and to produce either the first or second echo signal into a second tomographic image using second processing conditions different from the first processing conditions; and
   a displaying unit configured to display both the first and second tomographic images at the same time.

2. The diagnostic ultrasound apparatus of claim 1, wherein the plurality of times of transmission is two times of transmission along each scanning direction.

3. The diagnostic ultrasound apparatus of claim 2, wherein the processing conditions include at least one of a reception gain, a dynamic range, a cut-off frequency and a bandwidth of an echo filter, and a frame-to-frame after-image processing, which are used in the producing unit.

4. The diagnostic ultrasound apparatus of claim 2, wherein the processing conditions include information indicating at least one of a correction processing technique and a color encoding technique performed when intensities of the echo signals are mapped for display by the displaying unit.

5. The diagnostic ultrasound apparatus of claim 1, wherein the displaying unit has means for displaying the first and second tomographic images in mutually different colors.

6. The diagnostic ultrasound apparatus of claim 1, wherein the displaying unit has means for displaying the first and second tomographic images on a superposition basis one on another.

7. The diagnostic ultrasound apparatus of claim 6, wherein the displaying unit has means for displaying one tomographic image based on the difference signal superposed on the other tomographic image based on either the first or second echo signal.

8. The diagnostic ultrasound apparatus of claim 7, wherein the displaying unit has means for displaying either one of the first and second tomographic images in gray scales and a remaining tomographic image in colors.

9. The diagnostic ultrasound apparatus of claim 7, wherein the displaying unit has means for displaying the one and other tomographic images in mutually different colors.

10. The diagnostic ultrasound apparatus of claim 7, wherein the displaying unit has superposition control means changeable in a superposition balance of intensity of the first and second tomographic images displayed on the superposition basis.

11. The diagnostic ultrasound apparatus of claim 10, wherein the superposition control unit has manual-change commanding means capable of manually changing the superposition balance.

12. The diagnostic ultrasound apparatus of claim 1, wherein the displaying unit has means for displaying the first and second tomographic images in parallel with each other.

13. The diagnostic ultrasound apparatus of claim 1, wherein the producing unit has image memorizing means capable of individually memorizing image data of the first and second tomographic images and individually reading out the image data thereof.

14. The diagnostic ultrasound apparatus of claim 13, wherein the displaying unit has means for individually reading out the image data of the first and second tomographic images from the image memorizing means, and means for commanding a switchover of display modes consisting of superposed display of the first and second tomographic images, parallel display of the first and second tomographic images, and sole display of either one of the first and second tomographic images on the bases on the read-out image data.

15. The diagnostic ultrasound apparatus of claim 14, wherein the displaying unit includes means for independently selecting at least one of a correction processing technique and a color encoding technique in accordance with which of the echo signal and the difference signal corresponds to the read-out image data and means for mapping the image data on a video screen based on the selected technique.

16. The diagnostic ultrasound apparatus of claim 1, wherein the ultrasound contrast agent is a contrast agent of which main constituent is microbubbles, and the scanning unit has means for additionally transmitting an ultrasound signal to excite the microbubbles in each scanning direction.

17. The diagnostic ultrasound apparatus of claim 1, wherein the additional transmission of the exciting ultrasound signal interleaves in time between the two times of transmission of the ultrasound signal.

18. The diagnostic ultrasound apparatus of claim 1, wherein the displaying unit has means for commanding a switchover of display modes consisting of superposed display of the first and second tomographic images, parallel display of the first and second tomographic, and sole display of either one of the first and second tomographic images.

19. The diagnostic ultrasound apparatus of claim 1, wherein the producing unit includes a receiver in which detection is carried out toward the echo signals, wherein the ultrasound signal to be transmitted is formed into the radio frequency signal and the echo signal experiencing the subtraction executed by the subtraction unit is an echoed signal of the radio frequency signal which has yet to be subjected to the detection in the receiver.

20. The diagnostic ultrasound apparatus of claim 1, wherein scanning unit is configured to successively transmit the ultrasound signal the plurality of times in each scanning direction.

21. A diagnostic ultrasound apparatus for obtaining an image of a region to be scanned by scanning an object with a beam-shaped ultrasound signal produced as a radio frequency signal, an ultrasound contrast agent being injected into the object, the apparatus comprising:
   a scanning unit configured to transmit the ultrasound signal a plurality of times in each scanning direction along the region to be scanned and to receive an echo signal generated from the object in response to each time of transmission of the ultrasound signal in each scanning direction;
   a subtracting unit configured to obtain a difference signal by performing subtraction between first and second echo signals each still being the radio frequency signal, the first and second echo signals being from the plurality of echo signals received in response to the transmission of the ultrasound signal mt he same scanning direction;
   an adding unit configured to obtain an average signal by performing average between the first and second echo signals;
   a producing unit configured to produce the difference signal into a first tomographic image by a rate subtraction imaging technique and to produce the average signal into a second tomographic image; and
   a displaying unit configured to display both the first and second tomographic images at the same time.

22. The diagnostic ultrasound apparatus of claim 21, wherein the plurality of times of transmission is two times of transmission along each scanning direction.

23. The diagnostic ultrasound apparatus of claim 22, wherein the producing unit includes processing means for processing, into image data of the first and second tomographic images, the average signal and the difference signal under processing conditions mutually independent of each other.

24. The diagnostic ultrasound apparatus of claim 21, wherein the displaying unit has means for displaying the first and second tomographic images in either a superposition manner or a parallel manner.

25. The diagnostic ultrasound apparatus of claim 21, wherein the subtracting unit has means for performing the subtraction between the first echo signal received in response to the first transmission of the plurality of times of transmission of the ultrasound signal along each scanning line and the second echo signal received in response to a transmission carried out after the first transmission of the plurality of times of transmission of the ultrasound signal along each scanning line, and
   the adding unit has means for performing the addition between the first echo signal received in response to the first transmission of the plurality of times of transmission of the ultrasound signal along each scanning line and the second echo signal received in response to a transmission carried out after the first transmission of the plurality of times of transmission of the ultrasound signal along each scanning line.

26. The diagnostic ultrasound apparatus of claim 21, wherein scanning unit is configured to successively transmit the ultrasound signal the plurality of times in each scanning direction.

27. An ultrasound imaging method of obtaining an image of a region to be scanned by scanning an object with a beam-shaped ultrasound signal produced as a radio frequency signal, an ultrasound contrast agent being injected into the object, comprising the steps of:
   transmitting the ultrasound signal a plurality of times in each scanning direction along the region to be scanned and receiving an echo signal generated from the object in response to each time of transmission of the ultrasound signal in each scanning direction;
   obtaining a difference signal by performing subtraction between first and second echo signals each still being the radio frequency signal, the first and second echo signals being from the plurality of echo signals received in response to the transmission of the ultrasound signal in the same scanning direction;
   producing the difference signal into a first tomographic image by a rate subtraction imaging technique using first processing conditions and producing either the first or second echo signal into a second tomographic image using second processing conditions different from the first processing conditions; and
   displaying both the first and second tomographic images at the same time.

28. The ultrasound imaging method of claim 27, wherein in the transmitting step, the ultrasound is successively transmitted the plurality of times in each scanning direction.

29. An ultrasound imaging method of obtaining an image of a region to be scanned by scanning an object with a beam-shaped ultrasound signal produced as a radio frequency signal, an ultrasound contrast agent being injected into the object, comprising the steps of:
   transmitting the ultrasound signal a plurality of times in each scanning direction along the region to be scanned and receiving an echo signal generated from the object in response to each time of transmission of the ultrasound signal in each scanning direction;
   calculating a difference signal by performing subtraction between first and second echo signals each still being the radio frequency signal and calculating an average signal by performing average between the first and second echo signals, the first and second echo signals being from the plurality of echo signals received in response to the transmission of the ultrasound signal in the same scanning direction;
   producing the difference signal into a first tomographic image by a rate subtraction imaging technique and producing the average signal into a second tomographic image; and displaying both the first and second tomographic images at the same time.

30. The ultrasound imaging method of claim 29, wherein in the transmitting step, the ultrasound signal is successively transmitted the plurality of times in each scanning direction.

31. A diagnostic ultrasound apparatus for obtaining an image of a region to be scanned by scanning an object with a beam-shaped ultrasound signal produced as a radio frequency signal, an ultrasound contrast agent being injected into the object, the apparatus comprising:

an ultrasound probe configured to transmit and receive the ultrasound signal;

a transmitter configured to excite the ultrasound probe responsively to each of a plurality of rate pulses so as to cause the ultrasound probe to output the ultrasound signal;

a receiver configured to delay and add an echo signal received by the ultrasound probe;

a controller configured to cause the transmitter to transmit the ultrasound signal a plurality of times in each scanning direction along the region to be scanned and to cause the receiver to receive the echo signal generated from the object in response to each of the plurality of times of transmission of the ultrasound signal in each scanning direction;

a subtracter configured to obtain a difference signal by performing subtraction between first and second echo signals each still being the radio frequency signal, the first and second echo signals being from the plurality of echo signals received in response to the transmission of the ultrasound signal in the same scanning direction;

a producer configured to produce the difference signal into a first tomographic image by a rate subtraction imaging technique using first processing conditions and to produce either the first or second echo signal into a second tomographic image using second processing conditions different from the first processing conditions; and a display configured to display both the first and second tomographic images at the same time.

32. The diagnostic ultrasound apparatus of claim 31, wherein the plurality of times of transmission is two times of transmission along each scanning direction.

33. The diagnostic ultrasound apparatus of claim 31, wherein the display is configured to display the first and second tomographic images on a superposition basis one on another.

34. The diagnostic ultrasound apparatus of claim 33, wherein the display is configured to be changeable in a superposition balance of intensity of the first and second tomographic images displayed on the superposition basis.

35. The diagnostic ultrasound apparatus of claim 34, wherein the display is configured to be capable of manually changing the superposition balance.

36. The diagnostic ultrasound apparatus of claim 31, wherein the ultrasound signal to be transmitted is formed into the radio frequency signal and the echo signal experiencing the subtraction executed by the subtracter is an echoed signal of the radio frequency signal which has yet to be subjected to detection carried out in the receiver.

37. A diagnostic ultrasound apparatus for obtaining an image of a region to be scanned by scanning an object with a beam-shaped ultrasound signal produced as a radio frequency signal, an ultrasound contrast agent being injected into the object, the apparatus comprising:

scanning means for transmitting the ultrasound signal a plurality of times in each scanning direction along the region and receiving an echo signal generated from the object in response to each time of transmission of the ultrasound signal in each scanning direction;

subtracting means for obtaining a difference signal by performing subtraction between first and second echo signals each still being the radio frequency signal, the first and second echo signals being from the plurality of echo signals received in response to the transmission of the ultrasound signal in the same scanning direction;

producing means for producing the difference signal into a first tomographic image by a rate subtraction imaging technique using first processing conditions and for producing either the first or second echo signal into a second tomographic image using second processing conditions different from the first processing conditions; and displaying means for displaying both the first and second tomographic images at the same time.

38. A diagnostic ultrasound apparatus for obtaining an image of a region to be scanned by scanning an object with a beam-shaped ultrasound signal produced as a radio frequency signal, an ultrasound contrast agent being injected into the object, the apparatus comprising:

scanning means for transmitting the ultrasound signal a plurality of times in each scanning direction along the region and receiving an echo signal generated from the object in response to each time of transmission of the ultrasound signal in each scanning direction;

subtracting means for obtaining a difference signal by performing subtraction between first and second echo signals each still being the radio frequency signal, the first and second echo signals being from the plurality of echo signals received in response to the transmission of the ultrasound signal in the same scanning direction;

addition means for obtaining an average signal by performing average between the first and second echo signals;

producing mean for producing the difference signal into a first tomographic image by a rate subtraction imaging technique and producing the average signal into a second tomographic image; and displaying means for displaying both the first and second tomographic images at the same time.

* * * * *